(12) United States Patent
Hamauzu (10) Patent No.: US 11,978,549 B2
(45) Date of Patent: May 7, 2024

(54) TRAINING IMAGE GENERATION DEVICE, TRAINING IMAGE GENERATION METHOD, TRAINING IMAGE GENERATION PROGRAM, LEARNING DEVICE, LEARNING METHOD, LEARNING PROGRAM, DISCRIMINATOR, RADIOGRAPHIC IMAGE PROCESSING DEVICE, RADIOGRAPHIC IMAGE PROCESSING METHOD, AND RADIOGRAPHIC IMAGE PROCESSING PROGRAM

(71) Applicant: FUJIFILM Corporation, Tokyo (JP)

(72) Inventor: Shin Hamauzu, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 193 days.

(21) Appl. No.: 17/160,910

(22) Filed: Jan. 28, 2021

(65) Prior Publication Data

US 2021/0241039 A1 Aug. 5, 2021

(30) Foreign Application Priority Data

Feb. 5, 2020 (JP) .................. 2020-017709

(51) Int. Cl.
*G16H 30/40* (2018.01)
*A61B 6/00* (2006.01)
(Continued)

(52) U.S. Cl.
CPC ............... *G16H 30/40* (2018.01); *A61B 6/12* (2013.01); *A61B 6/5247* (2013.01);
(Continued)

(58) Field of Classification Search
CPC ......... A61B 34/20; A61B 6/12; A61B 6/5247; A61B 6/5282; A61F 13/44; G06N 3/08;
(Continued)

(56) References Cited

U.S. PATENT DOCUMENTS 9,792,682 B2 * 10/2017 Gluncic .................. G16H 30/40
10,278,587 B2 * 5/2019 Grenon ................ A61B 5/0077
(Continued)

FOREIGN PATENT DOCUMENTS

JP 2006-506117 A 2/2006
JP 2017-185007 A 10/2017
(Continued)

OTHER PUBLICATIONS

I. Kompatsiaris et al., "Deformable Boundary Detection of Stents in Angiographic Images", IEEE Transactions on Medical Imaging, vol. 19, No. 6, Jun. 2000, pp. 652-662, DOI: 10.1109/42.870673.
(Continued)

*Primary Examiner* — Keith M Raymond
*Assistant Examiner* — Patrick M Mehl
(74) *Attorney, Agent, or Firm* — Studebaker & Brackett PC (57) ABSTRACT

A processor acquires a radiographic image including a human body and a surgical tool image which indicates a surgical tool and is acquired by a method other than radiography. The processor combines the surgical tool image with the radiographic image to generate a training image for training a discriminator that discriminates a region of the surgical tool in a target image in a case in which the target image is input.

15 Claims, 9 Drawing Sheets

(51) Int. Cl.
  *A61B 6/12* (2006.01)
  *A61B 34/20* (2016.01)
  *A61F 13/44* (2006.01)
  *G06F 18/214* (2023.01)
  *G06F 18/25* (2023.01)
  *G06N 3/08* (2023.01)
  *G06T 7/70* (2017.01)
  *G06V 10/764* (2022.01)
  *G06V 10/774* (2022.01)
  *G06V 10/82* (2022.01)
  *G16H 20/40* (2018.01)
  *G16H 40/63* (2018.01)

(52) U.S. Cl.
  CPC ............ *A61B 6/5282* (2013.01); *A61B 34/20* (2016.02); *A61F 13/44* (2013.01); *G06F 18/2148* (2023.01); *G06F 18/251* (2023.01); *G06N 3/08* (2013.01); *G06T 7/70* (2017.01); *G06V 10/764* (2022.01); *G06V 10/774* (2022.01); *G06V 10/82* (2022.01); *G16H 20/40* (2018.01); *G16H 40/63* (2018.01); *G06T 2207/10116* (2013.01); *G06T 2207/20081* (2013.01); *G06T 2207/30004* (2013.01); *G06V 2201/034* (2022.01)

(58) Field of Classification Search
  CPC . G06T 2207/10116; G06T 2207/20081; G06T 2207/30004; G06T 7/70; G16H 20/40; G16H 30/40; G16H 40/63
  See application file for complete search history.

(56) References Cited

U.S. PATENT DOCUMENTS

| | | | |
|---|---|---|---|
| 2006/0058643 | A1 | 3/2006 | Florent et al. |
| 2007/0219516 | A1* | 9/2007 | Patel .................... A61F 13/44 604/362 |
| 2016/0071264 | A1* | 3/2016 | Agam .................. G06V 10/774 382/128 |
| 2016/0278731 | A1* | 9/2016 | Babic .................... A61B 6/547 |
| 2018/0008352 | A1 | 1/2018 | Flexman et al. |
| 2018/0113083 | A1* | 4/2018 | Van Dael ............ G01N 23/046 |
| 2020/0005472 | A1 | 1/2020 | Terunuma et al. |
| 2021/0030374 | A1 | 2/2021 | Takahashi et al. |

FOREIGN PATENT DOCUMENTS

| | | |
|---|---|---|
| JP | 2018-502646 A | 2/2018 |
| JP | 2018-068863 A | 5/2018 |
| WO | 2018/159775 A1 | 9/2018 |
| WO | 2019/138438 A1 | 7/2019 |

OTHER PUBLICATIONS

An Office Action; "Notice of Reasons for Refusal," mailed by the Japanese Patent Office dated Feb. 7, 2023, which corresponds to Japanese Patent Application No. 2020-017709 and is related to U.S. Appl. No. 17/160,910; with English language translation.

An Office Action; "Decision of Refusal," mailed by the Japanese Patent Office dated Jul. 4, 2023, which corresponds to Japanese Patent Application No. 2020-017709 and is related to U.S. Appl. No. 17/160,910; with English language translation.

* cited by examiner

TRAINING IMAGE GENERATION DEVICE, TRAINING IMAGE GENERATION METHOD, TRAINING IMAGE GENERATION PROGRAM, LEARNING DEVICE, LEARNING METHOD, LEARNING PROGRAM, DISCRIMINATOR, RADIOGRAPHIC IMAGE PROCESSING DEVICE, RADIOGRAPHIC IMAGE PROCESSING METHOD, AND RADIOGRAPHIC IMAGE PROCESSING PROGRAM

CROSS REFERENCE TO RELATED APPLICATIONS

The present application claims priority under 35 U.S.C. § 119 to Japanese Patent Application No. 2020-017709 filed on Feb. 5, 2020. The above application is hereby expressly incorporated by reference, in its entirety, into the present application.

BACKGROUND

Technical Field

The present disclosure relates to a training image generation device, a training image generation method, a training image generation program, a learning device, a learning method, a learning program, a discriminator, a radiographic image processing device, a radiographic image processing method, and a radiographic image processing program.

Related Art

Various surgical tools, such as gauze to suppress bleeding, a thread and a suture needle for sewing up a wound or an incision, a scalpel and scissors for incision, a drain for draining blood, and forceps for opening an incision, are used in a case in which a surgical operation is performed for a patient. The surgical tools may cause serious complications in a case in which they remain in the body of the patient after surgery. Therefore, it is necessary to check that no surgical tools remain in the body of the patient after surgery.

Therefore, a method has been proposed which prepares a discriminator that has learned the characteristics of a gauze image and inputs an image acquired by capturing a surgical field with a camera to the discriminator to discriminate whether or not gauze is present (see JP2018-068863A).

However, since gauze is stained with blood, it is difficult to find gauze in the image acquired by the camera even in a case in which the discriminator is used. Further, a small surgical tool, such as a suture needle, is likely to go between the internal organs. Therefore, it is difficult to find the surgical tool in the image acquired by the camera even in a case in which the discriminator is used. In contrast, it is considered that a radiographic image of the patient is acquired after surgery and is observed to check whether or not a surgical tool remains in the body of the patient. However, since both the operator and the nurse are tired after long surgery, the possibility of missing the remaining surgical tools is high. In addition, since the radiographic image which includes a surgical tool, such as gauze, and is necessary for training the discriminator is extremely rare, it is difficult to collect a large number of radiographic images for training the discriminator.

SUMMARY OF THE INVENTION

The present disclosure has been made in view of the above-mentioned problems and an object of the present disclosure is to provide a technique that can reliably prevent a surgical tool from remaining in the body of a patient after surgery.

According to the present disclosure, there is provided a training image generation device comprising at least one processor. The processor is configured to acquire a radiographic image including a human body and a surgical tool image which indicates a surgical tool and is acquired by a method other than radiography and to combine the surgical tool image with the radiographic image to generate a training image for training a discriminator that discriminates a region of the surgical tool in a target image in a case in which the target image is input.

The "method other than radiography" means a method other than the method which irradiates the surgical tool with radiation and detects the radiation transmitted through the surgical tool to acquire an image. Specifically, a generation method using computer graphics and a photography method are given as examples.

Further, in the training image generation device according to the present disclosure, the processor may be configured to combine the radiographic image and the surgical tool image using combination parameters corresponding to characteristics of the surgical tool to generate the training image.

Furthermore, in the training image generation device according to the present disclosure, the processor may be configured to set the combination parameters according to at least one of radiation absorptivity of the surgical tool, a degree of scattering of radiation in the radiographic image, beam hardening in the radiographic image, or noise corresponding to imaging conditions of the radiographic image.

Moreover, in the training image generation device according to the present disclosure, the surgical tool may include at least one of gauze, a scalpel, scissors, a drain, a suture needle, a thread, forceps, or a stent graft.

In this case, at least a portion of the gauze may include a radiation absorbing thread.

According to the present disclosure, there is provided a learning device comprising at least one processor. The processor is configured to train a discriminator that discriminates a region of a surgical tool in an input radiographic image, using a large number of training data items consisting of a training image generated by the training image generation device according to the present disclosure and correct answer data indicating the region of the surgical tool in the training image.

According to the present disclosure, there is provided a discriminator that is trained by the learning device according to the present disclosure.

According to the present disclosure, there is provided a radiographic image processing device comprising at least one processor. The processor is configured to discriminate the region of the surgical tool in the input radiographic image using the discriminator according to the present disclosure to detect the region of the surgical tool.

In addition, in the radiographic image processing device according to the present disclosure, the processor may be configured to display a detection result of the region of the surgical tool on a display screen.

According to the present disclosure, there is provided training data that consists of a training image generated by the training image generation device according to the present disclosure and correct answer data indicating the region of the surgical tool in the training image and is used for training a discriminator that discriminates the region of the surgical tool in an input radiographic image.

According to the present disclosure, there is provided a training image generation method comprising: acquiring a radiographic image including a human body and a surgical tool image which indicates a surgical tool and is acquired by a method other than radiography; and combining the surgical tool image with the radiographic image to generate a training image for training a discriminator that discriminates a region of the surgical tool in a target image in a case in which the target image is input.

According to the present disclosure, there is provided a learning method for training a discriminator that discriminates a region of a surgical tool in an input radiographic image, using a large number of training data items consisting of a training image generated by the training image generation device according to the present disclosure and correct answer data indicating the region of the surgical tool in the training image.

According to the present disclosure, there is provided a radiographic image processing method for discriminating the region of the surgical tool in the input radiographic image using the discriminator according to the present disclosure to detect the region of the surgical tool.

In addition, programs that cause a computer to perform the training image generation method, the learning method, and the radiographic image processing method according to the present disclosure may be provided.

According to the present disclosure, it is possible to reliably prevent a surgical tool from remaining in the body of a patient after surgery.

DETAILED DESCRIPTION

Figure 1:
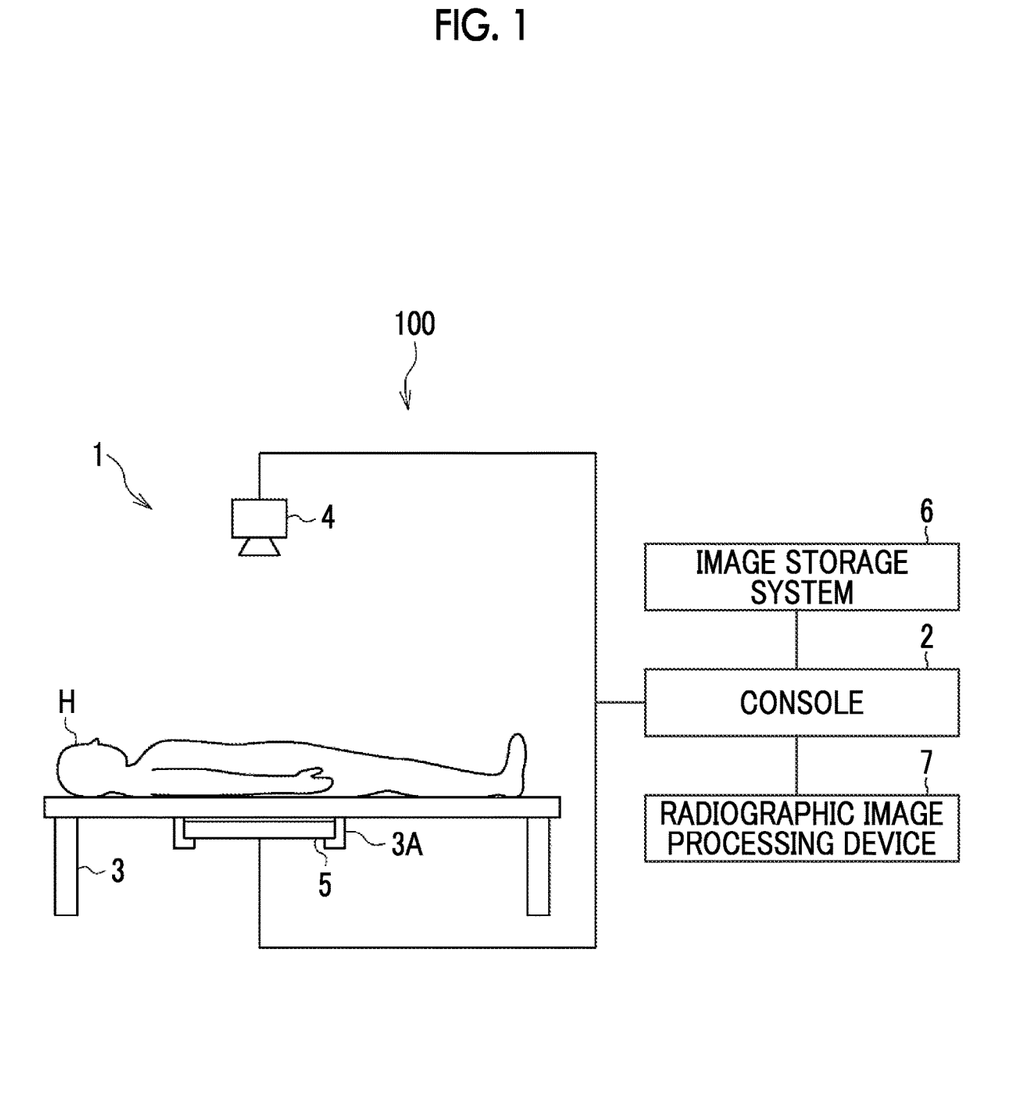
FIG. 1 is a block diagram schematically illustrating a configuration of a radiography system to which a radiographic image processing device according to an embodiment of the present disclosure is applied.

Hereinafter, embodiments of the present disclosure will be described with reference to the drawings. FIG. 1 is a block diagram schematically illustrating a configuration of a radiography system to which a radiographic image processing device according to an embodiment of the present disclosure is applied. As illustrated in FIG. 1, a radiography system 100 according to this embodiment acquires a radiographic image of a subject that is a patient after a surgical operation and detects a surgical tool included in the radiographic image. The radiography system 100 according to this embodiment comprises an imaging apparatus 1, a console 2, an image storage system 6, and a radiographic image processing device 7.

The imaging apparatus 1 detects radiation, which has been emitted from a radiation source 4, such as an X-ray source, and transmitted through a subject H, with a radiation detector 5 to acquire a radiographic image G0 of the subject H that lies supine on an operating table 3. The radiographic image G0 is input to the console 2.

The radiation detector 5 is a portable radiation detector and is attached to the operating table 3 by an attachment portion 3A that is provided in the operating table 3. In addition, the radiation detector 5 may be fixed to the operating table 3.

The console 2 has a function of controlling the imaging apparatus 1 using, for example, an imaging order and various kinds of information acquired from a radiology information system (RIS) (not illustrated) or the like through a network, such as a wireless communication local area network (LAN), and commands or the like directly issued by an engineer or the like. For example, in this embodiment, a server computer is used as the console 2.

The image storage system 6 is a system that stores image data of the radiographic images captured by the imaging apparatus 1. The image storage system 6 extracts an image corresponding to a request from, for example, the console 2 and the radiographic image processing device 7 from the stored radiographic images and transmits the image to a device that is the source of the request. A specific example of the image storage system 6 is a picture archiving and communication system (PACS).

Next, the radiographic image processing device according to this embodiment will be described. In addition, the radiographic image processing device 7 according to this embodiment includes a training data generation device and a learning device according to the present disclosure. In the following description, it is assumed that the radiographic image processing device represents these devices.

Figure 2:
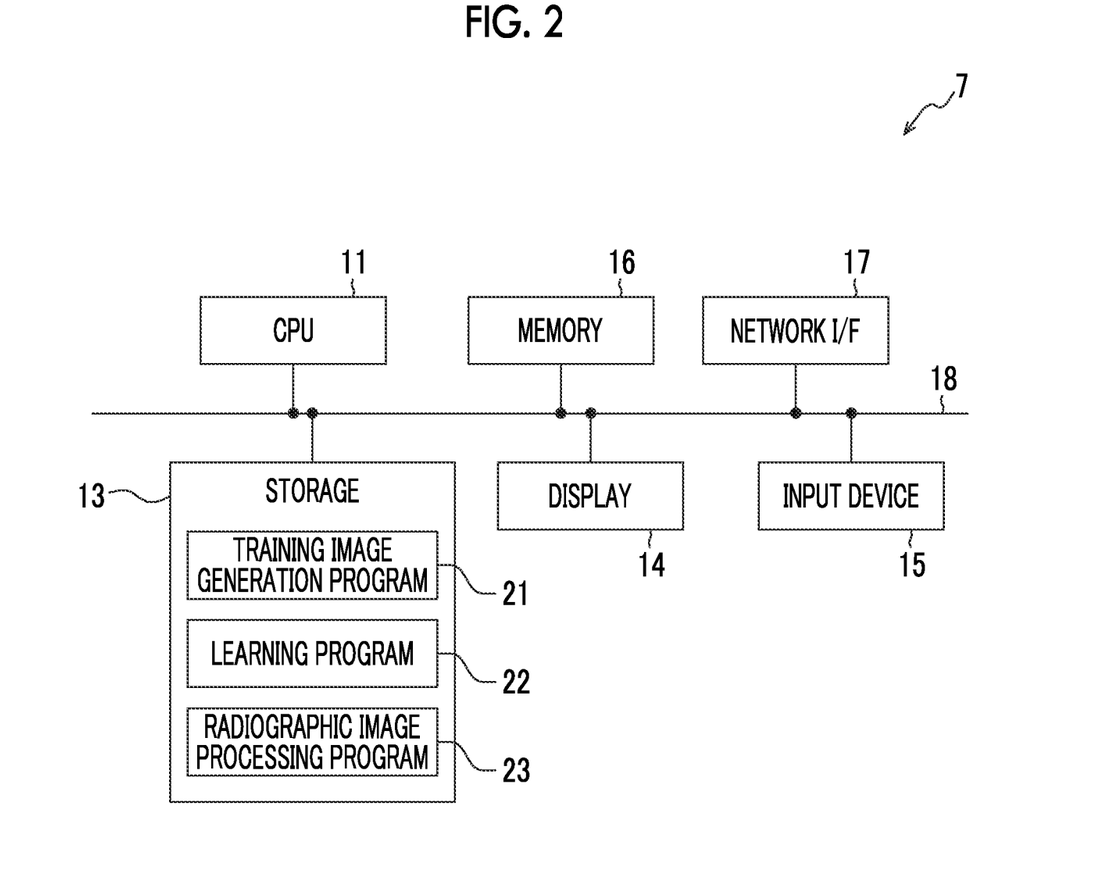
FIG. 2 is a diagram schematically illustrating a configuration of the radiographic image processing device according to this embodiment.

First, the hardware configuration of the radiographic image processing device according to this embodiment will be described with reference to FIG. 2. As illustrated in FIG. 2, the radiographic image processing device 7 is a computer, such as a workstation, a server computer, or a personal computer, and comprises a central processing unit (CPU) 11, a non-volatile storage 13, and a memory 16 as a temporary storage area. In addition, the radiographic image processing device 7 comprises a display 14, such as a liquid crystal display, an input device 15, such as a keyboard and a mouse, and a network interface (I/F) 17 that is connected to a network 10. The CPU 11, the storage 13, the display 14, the input device 15, the memory 16, and the network OF 17 are connected to a bus 18. The CPU 11 is an example of a processor according to the present disclosure.

The storage 13 is implemented by, for example, a hard disk drive (HDD), a solid state drive (SSD), and a flash memory. The storage 13 as a storage medium stores a training image generation program 21, a learning program 22, and a radiographic image processing program 23 which are installed in the radiographic image processing device 7. The CPU 11 reads out the training image generation program 21, the learning program 22, and the radiographic image processing program 23 from the storage 13, expands the programs in the memory 16, and executes the expanded training image generation program 21, learning program 22, and radiographic image processing program 23.

In addition, the training image generation program 21, the learning program 22, and the radiographic image processing program 23 are stored in a storage device of a server computer connected to the network or a network storage so as to be accessed from the outside and are downloaded and installed in the computer forming the radiographic image processing device 7 on demand. Alternatively, the programs are recorded on a recording medium, such as a digital versatile disc (DVD) or a compact disc read only memory (CD-ROM), are distributed and installed in the computer forming the radiographic image processing device 7 from the recording medium.

Figure 3:
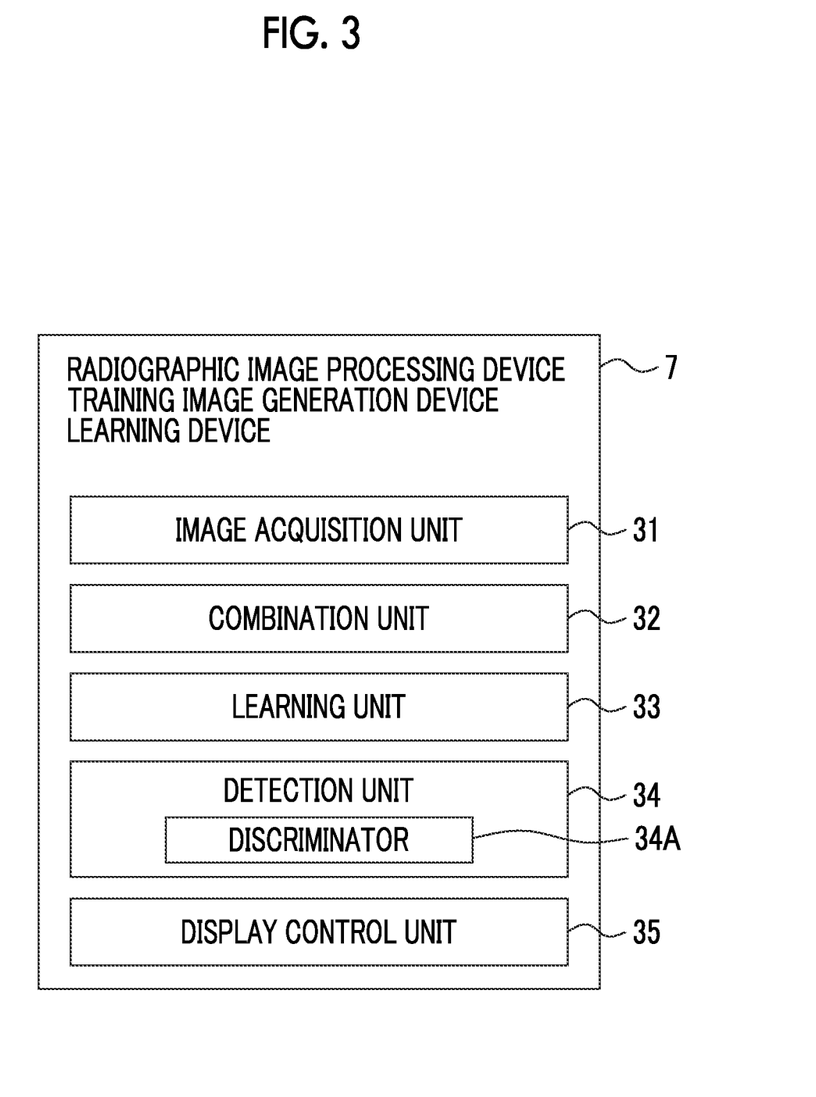
FIG. 3 is a diagram illustrating the functional configuration of the radiographic image processing device according to this embodiment.

Next, the functional configuration of the radiographic image processing device according to this embodiment will be described. FIG. 3 is a diagram schematically illustrating the functional configuration of the radiographic image processing device according to this embodiment. As illustrated in FIG. 3, the radiographic image processing device (the training image generation device and the learning device) 7 comprises an image acquisition unit 31, a combination unit 32, a learning unit 33, a detection unit 34, and a display control unit 35. Then, the CPU 11 executes the training image generation program 21, the learning program 22, and the radiographic image processing program 23 to function as the image acquisition unit 31, the combination unit 32, the learning unit 33, the detection unit 34, and the display control unit 35.

In addition, the image acquisition unit 31 and the combination unit 32 form the training image generation device according to this embodiment. The image acquisition unit 31 and the learning unit 33 form the learning device according to this embodiment. The image acquisition unit 31, the detection unit 34, and the display control unit 35 form the radiographic image processing device 7 according to this embodiment.

Figure 4:
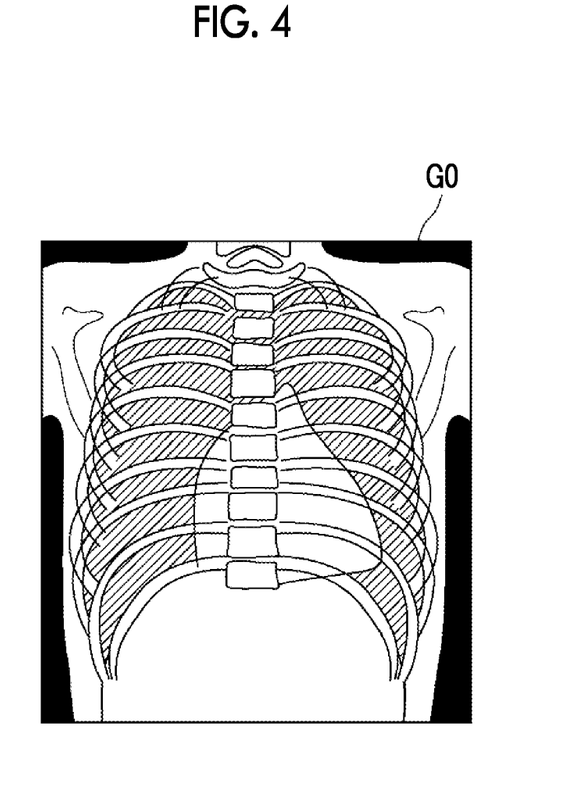
FIG. 4 is a diagram illustrating a radiographic image for generating a training image.

The image acquisition unit 31 acquires the radiographic image G0 including any subject H from the image storage system 6 through the network I/F 17 in order to generate a training image T0 which will be described below. FIG. 4 is a diagram illustrating the radiographic image G0. In addition, FIG. 4 illustrates the radiographic image of the chest of the human body. However, the subject included in the radiographic image G0 is not limited thereto.

Figure 5:
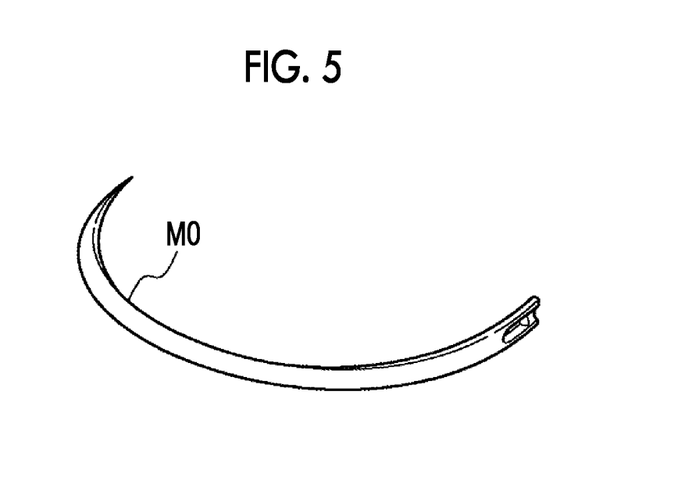
FIG. 5 is a diagram illustrating an image of a suture needle as a surgical tool.

Further, the image acquisition unit 31 acquires a surgical tool image M0 indicating a surgical tool from the image storage system 6 in order to generate the training image T0. The surgical tool image M0 is an image that is acquired by a method other than radiography. For example, the surgical tool image M0 is a three-dimensional image indicating a surgical tool which has been created by computer graphics or the like. In addition, in this embodiment, it is assumed that a suture needle for sewing up a wound or an incision is used as the surgical tool. FIG. 5 is a diagram illustrating the image of the suture needle as the surgical tool. In FIG. 5, the surgical tool image M0 of the suture needle is two-dimensionally illustrated. However, it is assumed that the surgical tool image M0 can be three-dimensionally rotated or moved. In addition, the surgical tool image M0 may be a photographic image of the surgical tool.

Further, the image acquisition unit 31 drives the radiation source 4 to irradiate the subject H that has undergone surgery with radiation and detects the radiation transmitted through the subject H using the radiation detector 5 to acquires a radiographic image G1 from which the surgical tool is to be detected. In this case, the image acquisition unit 31 sets imaging conditions, such as the type of target and filter used in the radiation source 4, an imaging dose, a tube voltage, and an SID.

The combination unit 32 combines the surgical tool image M0 with the radiographic image G0 to generate the training image T0 for training a discriminator that discriminates a region of the surgical tool in the radiographic image G1 in a case in which the target radiographic image G1 is input. The combination unit 32 combines the radiographic image G0 and the surgical tool image M0 with combination parameters corresponding to the characteristics of the surgical tool (the suture needle in this embodiment) to generate the training image T0. The combination unit 32 sets the combination parameters according to at least one of the radiation absorptivity of the surgical tool (the suture needle in this embodiment), the degree of scattering of radiation by the surgical tool, beam hardening in the radiographic image G0, or noise corresponding to the imaging conditions of the radiographic image G0.

In addition, the radiographic image G0 may be displayed on the display 14, and the position of the surgical tool image M0 and the orientation of the surgical tool image M0 in the radiographic image G0 may be designated by a command input by the operator through the input device 15.

Figure 6:
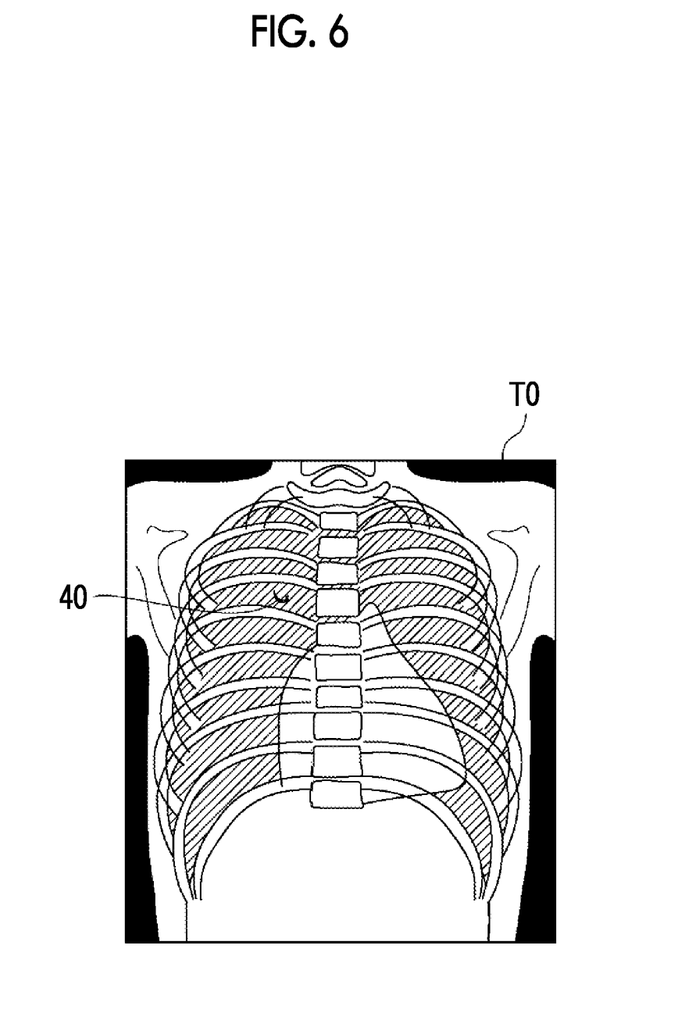
FIG. 6 is a diagram illustrating the training image.

In this embodiment, for example, it is assumed that the training image T0 is generated by the following Expression (1). That is, in pixels (x, y) of a region of the radiographic image G0 which is combined with the surgical tool image M0, a pixel value M0(x, y) of the surgical tool image M0 weighted by a weight coefficient w1 is subtracted from a pixel value G0(x, y) of the radiographic image G0 to derive a pixel value T0(x, y) of the training image T0. In addition, the weight coefficient w1 has a value that is equal to or greater than 0 and equal to or less than 1. The weight coefficient w1 is included in the combination parameters according to this embodiment. FIG. 6 is a diagram illustrating the training image. As illustrated in FIG. 6, in the training image T0, a suture needle 40 is included in the right lung of the subject.

$$T0(x,y)=G0(x,y)-w1\cdot M0(x,y) \qquad (1)$$

Here, in a case in which the radiation absorptivity of the surgical tool is high, the contrast of the surgical tool is high in a radiographic image acquired by performing radiography for the surgical tool. For example, in a case in which the surgical tool is a metal tool, such as a suture needle, scissors, or a scalpel, the contrast of the radiographic image of the surgical tool is high. Therefore, in a case in which weighted subtraction between the radiographic image G0 and the surgical tool image M0 is performed, the weight coefficient w1 for the surgical tool image M0 is increased such that the contrast of the surgical tool is not too high in the training image T0.

Further, the contrast of the radiographic image is reduced due to the scattering of radiation. The influence of the scattering of radiation becomes larger as the body thickness of the subject H becomes larger. In addition, as the body thickness of the subject H becomes larger, the density of a subject region included in the radiographic image G0 becomes lower. Therefore, the combination unit 32 derives the average value of the density of the subject region included in the radiographic image G0, reduces the weight coefficient w1 such that a difference in density between the radiographic image G0 and the surgical tool image M0 becomes smaller as the average value become smaller, that is, the body thickness of the subject H becomes larger, and generates the training image T0.

Here, beam hardening occurs in which, as the tube voltage applied to the radiation source 4 becomes higher and the energy of radiation becomes higher, a lower-energy component of the radiation is absorbed by the subject H and the energy of the radiation becomes higher while the radiation is transmitted through the subject H. In a case in which the beam hardening occurs, the contrast of the radiographic image decreases. Further, the increase in the energy of radiation due to the beam hardening becomes more significant as the body thickness of the subject H becomes larger. In addition, as the body thickness of the subject H becomes larger, the density of a subject region included in the radiographic image G0 becomes lower. Therefore, the combination unit 32 derives the average value of the density of the subject region included in the radiographic image G0, reduces the weight coefficient w1 such that a difference in density between the radiographic image G0 and the surgical tool image M0 becomes smaller as the average value become smaller, that is, the body thickness of the subject H becomes larger, and generates the training image T0.

In addition, in a case in which the radiation dose in the imaging conditions is reduced, the amount of noise included in the radiographic image G0 increases. Therefore, in a case in which the radiation dose is small, the combination unit 32 adds noise N(x, y) corresponding to the radiation dose to Expression (1) to generate the training image T0, as represented by the following Expression (2). In this case, the weight coefficient w1 may be a predetermined value or may be set according to at least one of the radiation absorptivity of the surgical tool, the degree of scattering of radiation, or the beam hardening. Further, the noise N(x, y) may be derived by a predetermined simulation and may be stored in the storage 13. In addition, the noise N(x, y) is included in the combination parameters.

$$T0(x,y)=G0(x,y)-w1 \cdot M0(x,y)+N(x,y) \quad (2)$$

In this embodiment, the combination unit 32 changes the combination position of the surgical tool image M0 in the radiographic image G0 or the combination parameters to generate a plurality of training images T0 in order to train the discriminator which will be described below. Therefore, the training image T0 obtained by combining the surgical tool image M0 with the radiographic image G0 as if the surgical tool image M0 is acquired by radiography is generated. In addition, the training image T0 may be generated using a plurality of radiographic images G0 having different subjects H.

The learning unit 33 trains a discriminator 34A included in the detection unit 34 so as to discriminate the region of the surgical tool in the input radiographic image, using training data including the training image T0 and correct answer data in which the region of the surgical tool in the training image T0 is specified and training data consisting of a radiographic image without including the surgical tool. A plurality of training data items are prepared. In addition, a mask image obtained by masking the region of the surgical tool image M0 in a case in which the training image T0 is generated may be used as the correct answer data.

A machine learning model can be used as the discriminator 34A. One example of the machine learning model is a neural network model. Examples of the neural network model include a simple perceptron, a multilayer perceptron, a deep neural network, a convolutional neural network, a deep belief network, a recurrent neural network, and a stochastic neural network. In this embodiment, it is assumed that the convolutional neural network is used as the discriminator 34A.

Figure 7:
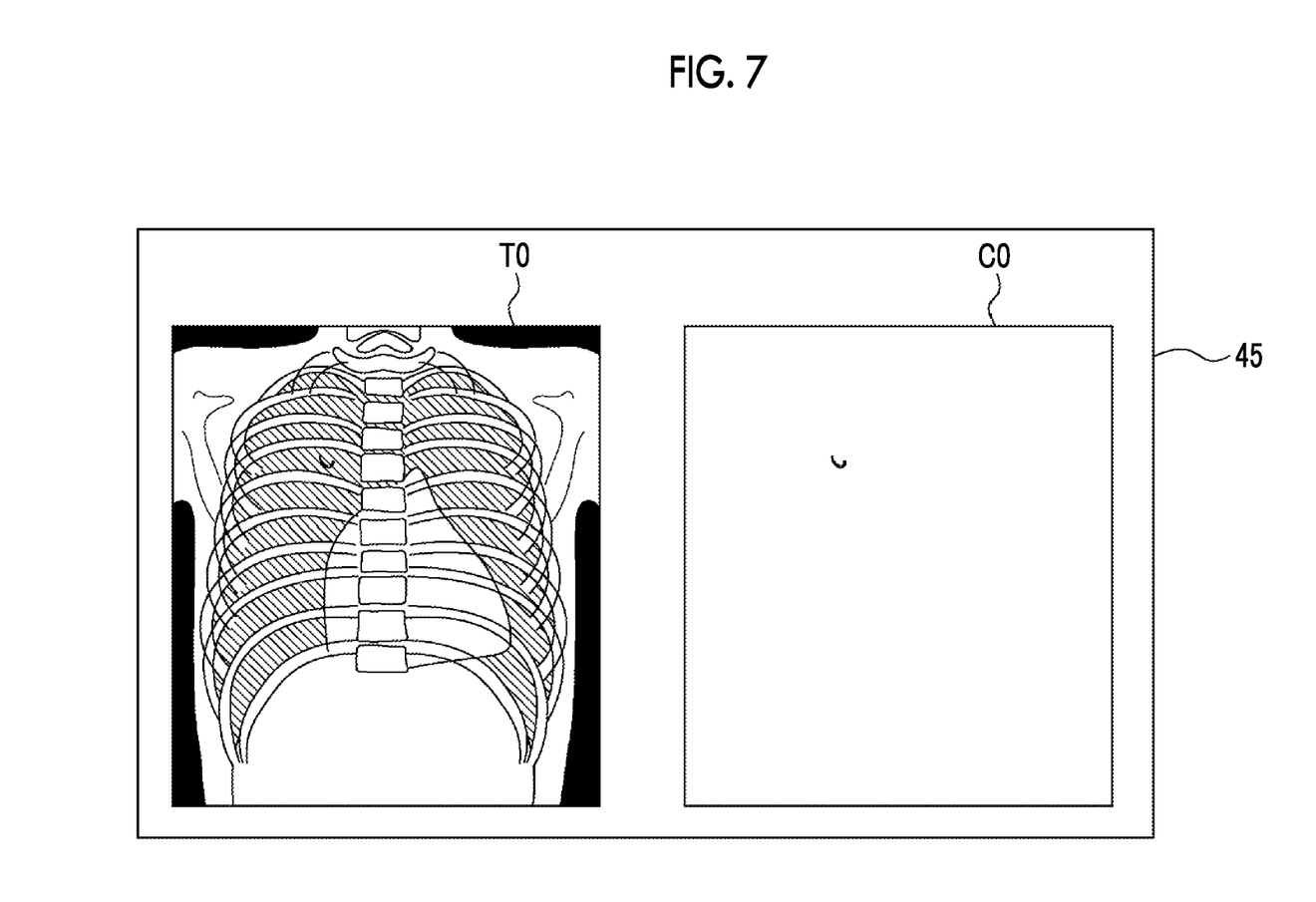
FIG. 7 is a diagram schematically illustrating training data.

FIG. 7 is a diagram schematically illustrating the training data including the training image T0 and the correct answer data in which the region of the surgical tool in the training image T0 is specified. As illustrated in FIG. 7, training data 45 includes the training image T0 including the surgical tool and correct answer data C0 in which the region of the surgical tool is specified.

In a case in which the training image T0 included in the training data is input, the discriminator 34A is trained so as to output the probability that each pixel of the training image T0 will be the region of the surgical tool. A region consisting of pixels having the probability which has been output from the discriminator 34A and is equal to or greater than a predetermined threshold value is the region of the surgical tool. The learning unit 33 inputs the training image T0 to the discriminator 34A and directs the discriminator 34A to output the probability of each pixel being the region of the surgical tool. Then, the difference between the region consisting of the pixels having the probability which has been output from the discriminator 34A and is equal to or greater than the predetermined threshold value and a region represented by the correct answer data included in the training data is derived as a loss. Then, the discriminator 34A is trained on the basis of the loss. Specifically, for example, a kernel coefficient in the convolutional neural network and a weight for the connection of neural networks are derived so as to reduce the loss. The learning unit 33 repeats learning until the loss is equal to or less than a predetermined threshold value. In this way, the discriminator 34A is trained such that a high probability equal to or greater than the predetermined threshold value is output for the region of the surgical tool included in the input radiographic image and the region of the surgical tool included in the input radiographic image is extracted.

The trained discriminator 34A is applied to the detection unit 34. In a case in which the target radiographic image G1 is input to the detection unit 34, the detection unit 34 directs the discriminator 34A to extract the region of the surgical tool included in the radiographic image G1 as a detection target, thereby detecting the region of the surgical tool.

Figure 8:
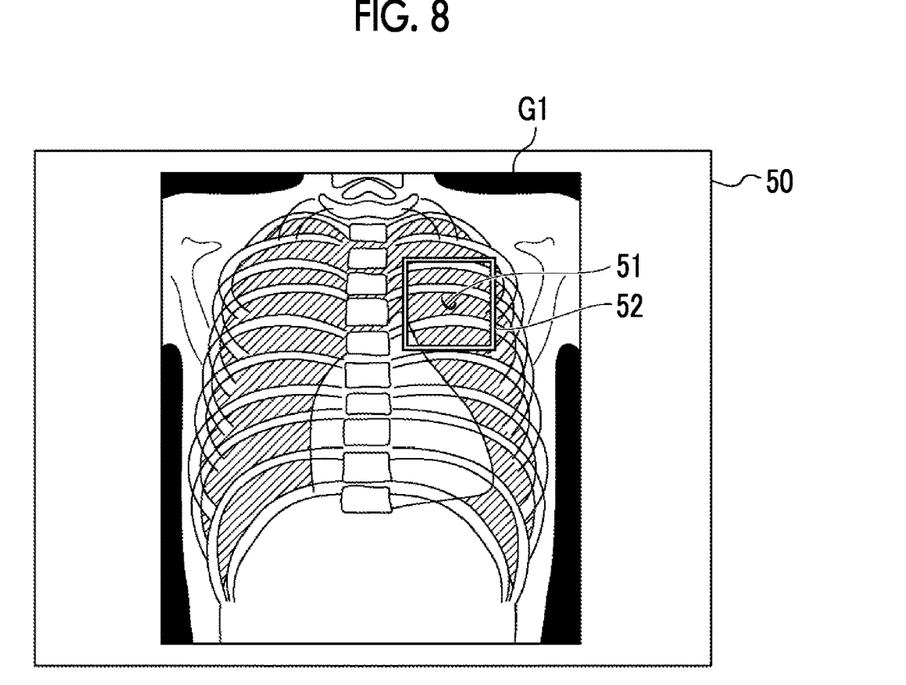
FIG. 8 is a diagram illustrating a radiographic image display screen.

The display control unit 35 displays the radiographic image G1 on the display 14 such that the region of the surgical tool detected from the radiographic image G1 as the detection target by the detection unit 34 is highlighted. FIG. 8 is a diagram illustrating a radiographic image display screen. As illustrated in FIG. 8, the radiographic image G1 is displayed on a display screen 50, and a surgical tool region 51 included in the radiographic image G1 is surrounded with a rectangular region 52 so as to be highlighted. In addition, the rectangular region 52 is illustrated in white in FIG. 8. However, the rectangular region 52 may be colored. Further, instead of giving the rectangular region 52, a mark, such as an arrow or an asterisk, may be given in the vicinity of the surgical tool region to highlight the surgical tool region.

Figure 9:
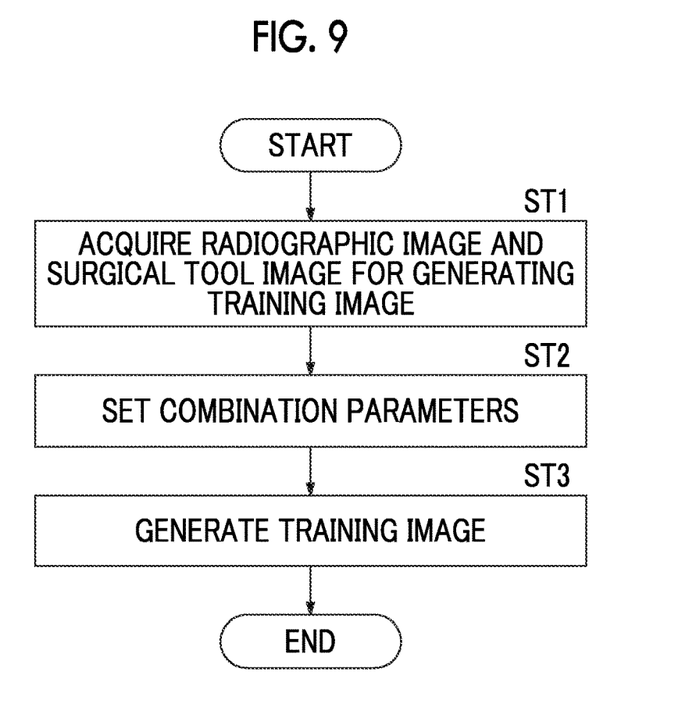
FIG. 9 is a flowchart illustrating a training image generation process according to this embodiment.

Next, a process performed in this embodiment will be described. FIG. 9 is a flowchart illustrating a training image generation process performed in this embodiment. First, the image acquisition unit 31 acquires the radiographic image G0 and the surgical tool image M0 for generating the training image T0 (Step ST1). Then, the combination unit 32 sets combination parameters for the radiographic image G0 and the surgical tool image M0 (Step ST2) and combines the radiographic image G0 and the surgical tool image M0 according to the combination parameters to generate the training image T0 (Step ST3). Then, the process ends.

Figure 10:
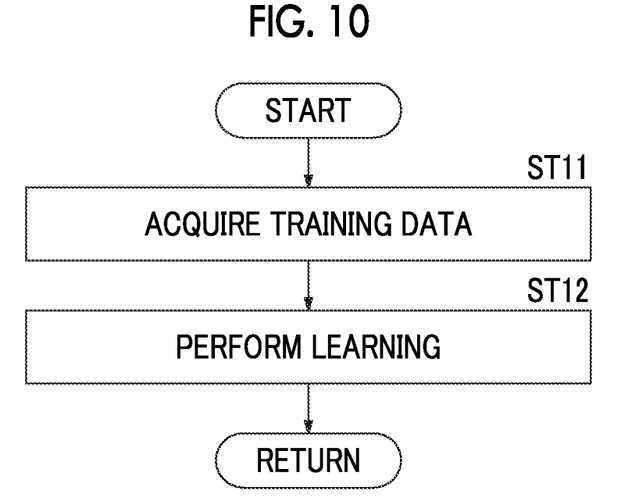
FIG. 10 is a flowchart illustrating a learning process according to this embodiment.

Next, a learning process according to this embodiment will be described. FIG. 10 is a flowchart illustrating the learning process performed in this embodiment. The learning unit 33 acquires training data consisting of the training image T0 and correct answer data, and training data consisting of a radiographic image without including the surgical tool (Step ST11), inputs the training data to the discriminator 34A, acquires the extraction result of the surgical tool region, trains the discriminator 34A using the loss based on the difference from the correct answer data (Step ST12), and returns to Step ST11. Then, the learning unit 33 repeats the process in Steps ST11 and ST12 until the loss reaches a predetermined threshold value, and ends the learning. In addition, the learning unit 33 may repeat the learning a predetermined number of times and end the learning.

Figure 11:
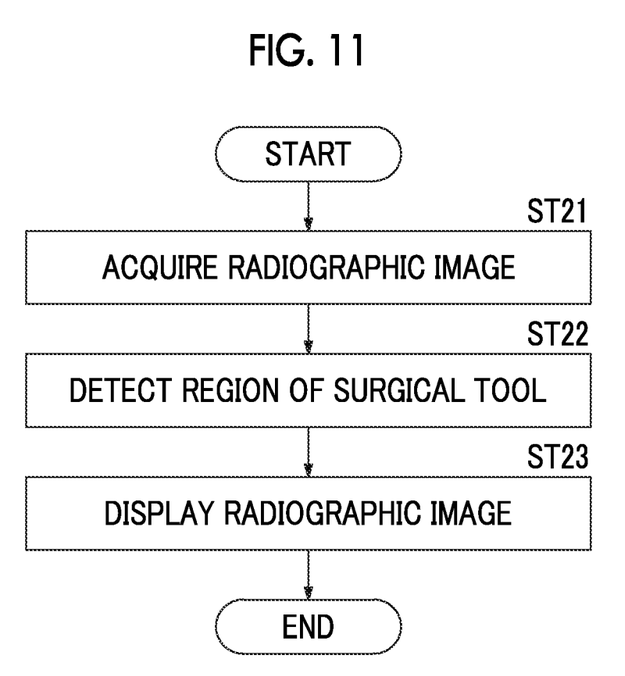
FIG. 11 is a flowchart illustrating a detection process according to this embodiment.

Next, a surgical tool region detection process according to this embodiment will be described. FIG. 11 is a flowchart illustrating the detection process performed in this embodiment. The image acquisition unit 31 acquires the radiographic image G1 as a detection target (Step ST21), and the detection unit 34 detects a surgical tool region from the radiographic image G1 (Step ST22). Then, the display control unit 35 displays the radiographic image G1 in which the surgical tool region has been highlighted on the display 14 (Step ST23). Then, the process ends.

As such, in this embodiment, the detection unit 34 comprises the discriminator 34A that has been trained so as to discriminate the surgical tool region from the input radiographic image on the basis of the training data consisting of the training image T0 generated by combining the radiographic image G0 and the surgical tool image M0 indicating the surgical tool and the correct answer data indicating the surgical tool region in the training image T0. Then, the discriminator 34A discriminates the surgical tool region in the input radiographic image G0 to detect the surgical tool region. Therefore, according to this embodiment, it is possible to reliably check whether or not a surgical tool remains in the body of the patient with reference to the detection result. As a result, according to this embodiment, it is possible to reliably prevent a surgical tool from remaining in the body of the patient after surgery.

In contrast, since the radiographic image which includes the surgical tool and is necessary for training the discriminator 34A is extremely rare, it is difficult to collect a large number of radiographic images for training the discriminator 34A. In this embodiment, the discriminator 34A is trained using the training image T0 generated by combining the radiographic image G0 and the surgical tool image M0 indicating the surgical tool acquired by a method other than radiography. Therefore, it is possible to prepare a sufficient number of training images T0. As a result, it is possible to construct the discriminator 34A with high surgical tool detection accuracy.

Further, the radiographic image G0 and the surgical tool image M0 are combined using the combination parameters to generate the training image T0. Therefore, it is possible to generate the teacher image T0 obtained by combining the surgical tool image M0 acquired by a method other than radiography with the radiographic image G0 as if the surgical tool image M0 is acquired by radiography. Therefore, it is not necessary to capture the image of the surgical tool using radiography in order to prepare the surgical tool image M0.

In the above-described embodiment, the suture needle as a surgical tool is the detection target. However, the present disclosure is not limited thereto. Any surgical tool used in surgery, such as gauze, a scalpel, scissors, a drain, a thread, forceps, or a stent graft, can be used as the detection target. In this case, the surgical tool image M0 including the surgical tool which is used to generate the training image T0 may be acquired by capturing the image of a target surgical tool. Further, the discriminator 34A may be trained so as to discriminate the target surgical tool. In addition, the discriminator 34A may be trained so as to detect a plurality of channels. In this case, it is possible to construct the discriminator 34A so as to discriminate not only one kind of surgical tool but also a plurality of kinds of surgical tools.

Figure 12:
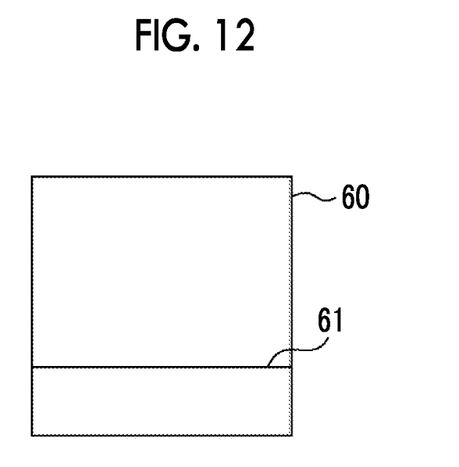
FIG. 12 is a diagram illustrating gauze.
Figure 13:
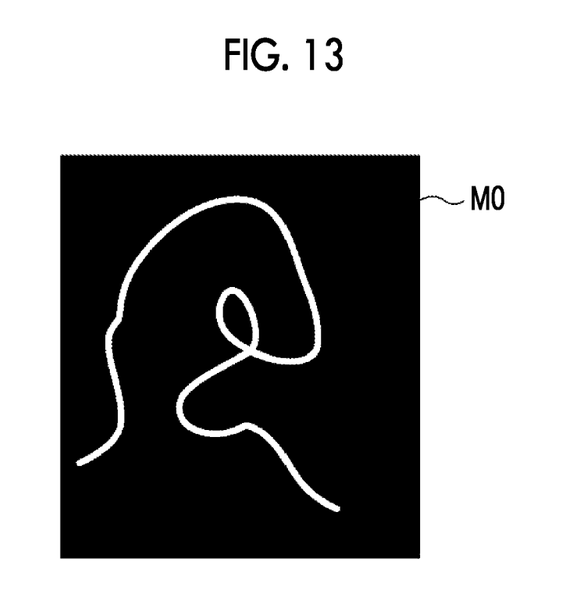
FIG. 13 is a diagram illustrating an image of gauze as the surgical tool.

Here, gauze used as the surgical tool will be described. FIG. 12 is a diagram illustrating gauze. As illustrated in FIG. 12, gauze 60 is a plain-woven cotton fabric and a radiation absorbing thread 61 is woven in a portion of the gauze 60. Cotton yarn transmits radiation and the radiation absorbing thread 61 absorbs radiation. Therefore, the radiographic image of the gauze 60 includes only the linear radiation absorbing thread 61. Here, during surgery, the gauze 60 is rolled and inserted into the human body in order to absorb blood. Therefore, an image indicating a state in which the radiation absorbing thread 61 is rolled is used as the surgical tool image M0 to be combined with the radiographic image G0 in order to generate the training image T0, as illustrated in FIG. 13.

In addition, in the above-described embodiment, the radiation is not particularly limited. For example, α-rays or γ-rays other than X-rays can be applied.

In the above-described embodiment, for example, the following various processors can be used as a hardware structure of processing units performing various processes, such as the image acquisition unit 31, the combination unit 32, the learning unit 33, the detection unit 34, and the display control unit 35. The various processors include, for example, a CPU which is a general-purpose processor executing software (program) to function as various processing units, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as the hardware structure.

Furthermore, specifically, an electric circuit (circuitry) obtained by combining circuit elements, such as semiconductor elements, can be used as the hardware structure of the various processors.

What is claimed is:

1. A training image generation device comprising:
at least one processor,
wherein the processor is configured to acquire a radiographic image G0 including a human body and a surgical tool image M0 which indicates a surgical tool and is acquired by a method other than radiography; and
combine the surgical tool image with the radiographic image by equation (1) using a weight coefficient w1, which is combination parameters corresponding to characteristics of the surgical tool to generate a training image T0(x, y) for training a discriminator that discriminates a region of the surgical tool in a target image in a case in which the target image is input, wherein the (x, y) is the pixel of the radiographic image G0 where the surgical tool image is combined,
wherein the weight coefficient w1, which is the combination parameters, is set so as to increase as radiation absorptivity of the surgical tool is higher, and is set so as to decrease as an average value of a density of a subject region included in the radiographic image is lower:

$$T0(x,y)=G0(x,y)-w1 \cdot M0(x,y) \qquad (1).$$

2. The training image generation device according to claim 1,
wherein the combination parameters are further set according to noise corresponding to imaging conditions of the radiographic image.

3. The training image generation device according to claim 1,
wherein the surgical tool includes at least one of gauze, a scalpel, scissors, a drain, a suture needle, a thread, forceps, or a stent graft.

4. The training image generation device according to claim 3,
wherein the surgical tool includes gauze wherein at least a portion of the gauze includes radiation absorbing thread.

5. A learning device comprising:
at least one processor,
wherein the processor is configured to train a discriminator that discriminates a region of a surgical tool in an input radiographic image, using a large number of training data items consisting of a training image generated by the training image generation device according to claim 1 and correct answer data indicating the region of the surgical tool in the training image.

6. A discriminator that is trained by the learning device according to claim 5.

7. A radiographic image processing device comprising:
at least one processor,
wherein the processor is configured to discriminate the region of the surgical tool in the input radiographic image using the discriminator according to claim 6 to detect the region of the surgical tool.

8. The radiographic image processing device according to claim 7,
wherein the processor is configured to display a detection result of the region of the surgical tool on a display screen.

9. A radiographic image processing method for discriminating the region of the surgical tool in the input radiographic image using the discriminator according to claim 6 to detect the region of the surgical tool.

10. A non-transitory computer-readable storage medium that stores a radiographic image processing program that causes a computer to perform:
a step of discriminating the region of the surgical tool in the input radiographic image using the discriminator according to claim 6 to detect the region of the surgical tool.

11. Training data that consists of a training image generated by the training image generation device according to claim 1 and correct answer data indicating the region of the surgical tool in the training image and is used for training a discriminator that discriminates the region of the surgical tool in an input radiographic image.

12. A learning method for training a discriminator that discriminates a region of a surgical tool in an input radiographic image, using a large number of training data items consisting of a training image generated by the training image generation device according to claim 1 and correct answer data indicating the region of the surgical tool in the training image.

13. A non-transitory computer-readable storage medium that stores a learning program that causes a computer to perform:
a step of training a discriminator that discriminates a region of a surgical tool in an input radiographic image, using a large number of training data items consisting of a training image generated by the training image generation device according to claim 1 and correct answer data indicating the region of the surgical tool in the training image.

14. A training image generation method comprising:
acquiring a radiographic image G0 including a human body and a surgical tool image M0 which indicates a surgical tool and is acquired by a method other than radiography; and
combining the surgical tool image with the radiographic image by equation (1) using a weight coefficient w1, which is combination parameters corresponding to characteristics of the surgical tool to generate a training image T0(x, y) for training a discriminator that discriminates a region of the surgical tool in a target image in a case in which the target image is input, wherein the (x, y) is the pixel of the radiographic image G0 where the surgical tool image is combined,
wherein the weight coefficient w1, which is the combination parameters, is set so as to increase as radiation absorptivity of the surgical tool is higher, and is set so as to decrease as an average value of a density of a subject region included in the radiographic image is lower:

$$T0(x,y)=G0(x,y)-w1 \cdot M0(x,y) \qquad (1).$$

15. A non-transitory computer-readable storage medium that stores a training image generation program that causes a computer to perform:
a step of acquiring a radiographic image G0 including a human body and a surgical tool image M0 which indicates a surgical tool and is acquired by a method other than radiography; and
a step of combining the surgical tool image with the radiographic image by equation (1) using a weight coefficient w1, which is combination parameters corresponding to characteristics of the surgical tool to generate a training image T0(x, y) for training a discriminator that discriminates a region of the surgical tool in a target image in a case in which the target image is input, wherein the (x, y) is the pixel of the radiographic image G0 where the surgical tool image is combined, wherein the weight coefficient w1, which is the combination parameters, is set so as to increase as radiation absorptivity of the surgical tool is higher, and is set so as to decrease as an average value of a density of a subject region included in the radiographic image is lower:

$$T0(x,y) = G0(x,y) - w1 \cdot M0(x,y) \qquad (1).$$

\* \* \* \* \*